United States Patent
Tüysüz et al.

(10) Patent No.: US 11,931,540 B1
(45) Date of Patent: Mar. 19, 2024

(54) ENHANCED PEN-LIKE PORTABLE DEVICE FOR CLEANING NEEDLE-FREE IV-CONNECTORS

(71) Applicant: Asset Medical International, Inc., San Diego, CA (US)

(72) Inventors: Mehmet Tüysüz, Mugla (TR); Ahmet Reha Basaran, Balikesir (TR)

(73) Assignee: Asset Medical International, Inc., San Diego, CA (US)

( * ) Notice: Subject to any disclaimer, the term of this patent is extended or adjusted under 35 U.S.C. 154(b) by 0 days.

(21) Appl. No.: 18/226,688

(22) Filed: Jul. 26, 2023

(51) Int. Cl.
  *A61M 39/16*  (2006.01)
  *A61M 5/32*   (2006.01)

(52) U.S. Cl.
  CPC ........ *A61M 39/162* (2013.01); *A61M 5/3202* (2013.01)

(58) Field of Classification Search
  CPC .......................... A61M 39/162; A61M 5/3202
  See application file for complete search history.

(56) References Cited

U.S. PATENT DOCUMENTS

| | | | |
|---|---|---|---|
| 3,987,930 A * | 10/1976 | Fuson ................... | A61M 39/20 206/508 |
| 4,572,373 A * | 2/1986 | Johansson .......... | B65D 77/2024 206/508 |
| 8,647,308 B2 | 2/2014 | Solomon et al. | |
| 8,777,504 B2 | 7/2014 | Shaw et al. | |
| 2008/0019889 A1 | 1/2008 | Rogers et al. | |
| 2009/0028750 A1 | 1/2009 | Ryan | |
| 2011/0044850 A1 | 2/2011 | Solomon et al. | |
| 2013/0019947 A1 | 1/2013 | Ejima et al. | |
| 2013/0197485 A1 * | 8/2013 | Gardner .............. | A61M 39/162 604/533 |
| 2014/0228773 A1 * | 8/2014 | Burkholz ............ | A61M 39/162 604/199 |
| 2016/0144118 A1 * | 5/2016 | Solomon ................. | A61M 5/30 206/370 |

FOREIGN PATENT DOCUMENTS

EP  3375472 B1  1/2021

OTHER PUBLICATIONS

European Search Report for application No. EP 17 16 1089 dated Sep. 21, 2017.

* cited by examiner

*Primary Examiner* — Dung T Ulsh
(74) *Attorney, Agent, or Firm* — Carter, DeLuca & Farrell LLP; George Likourezos

(57) ABSTRACT

The present disclosure proposes a pen-like assembly of caps for cleaning and protecting needle-free iv-connectors, with an extended shelf life. An enhanced gas-tightness in sealing is arranged in-between successively arranged caps that are engaged together. A first approach is based on enhancing geometric compliance between striking surfaces, by contacting one or more material components that have different respective Shore hardness values. A second approach is based on meandering and extending a possible fluid communication route from a cavity inside a cap towards surroundings of the assembly. A third approach includes the provision of the fluid communication route with an adhesive or sealant to achieve a gas-tight sealing. A fourth approach includes circumferentially covering junctions with one or more covers that are substantially gas impermeable.

20 Claims, 12 Drawing Sheets

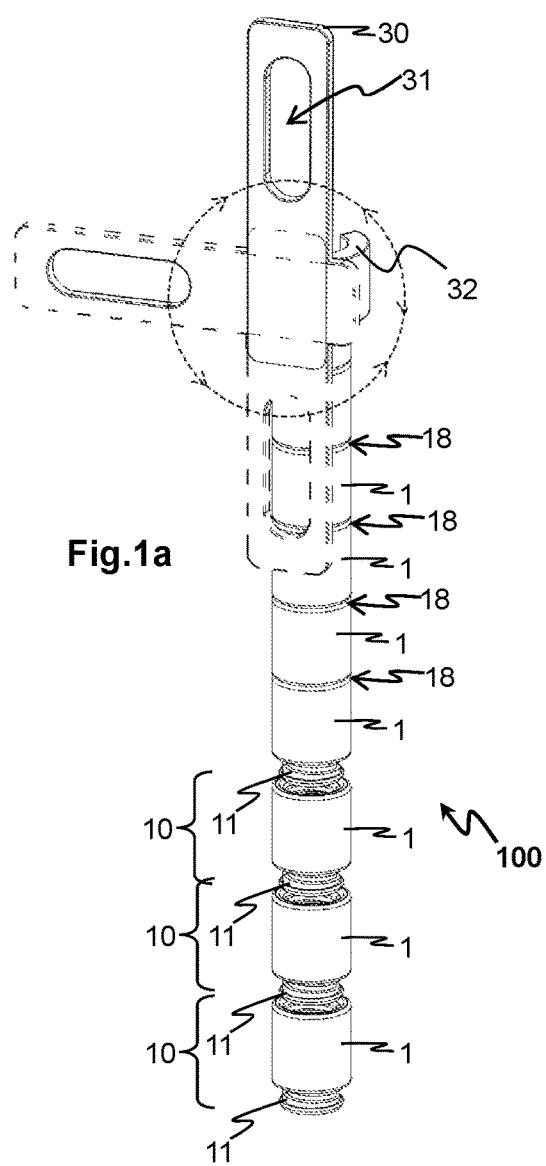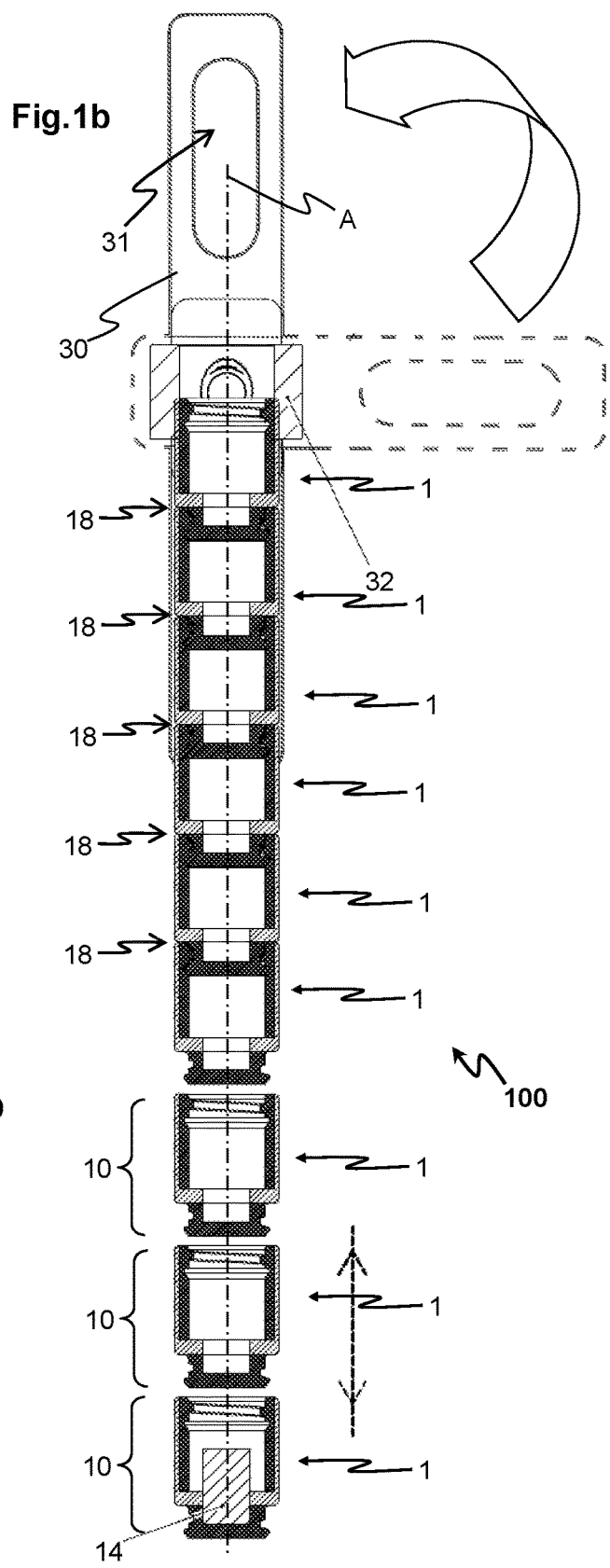

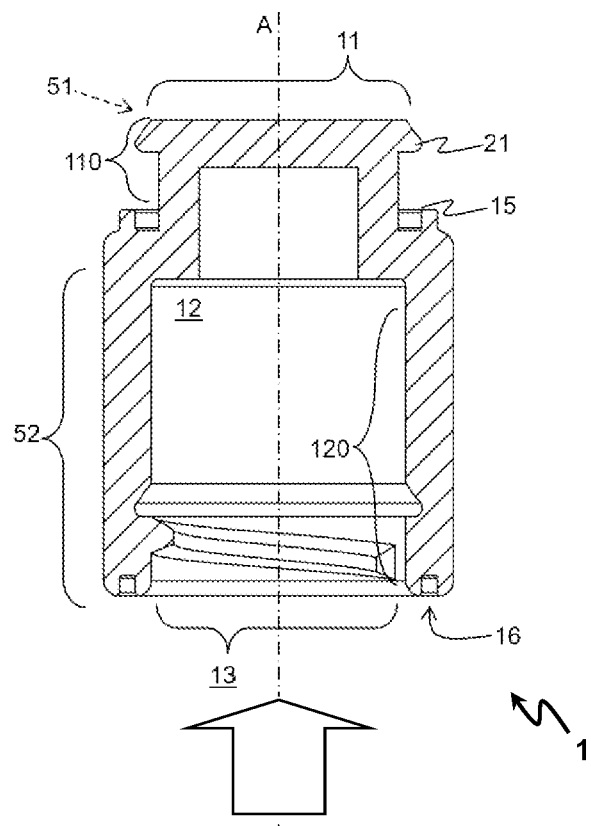
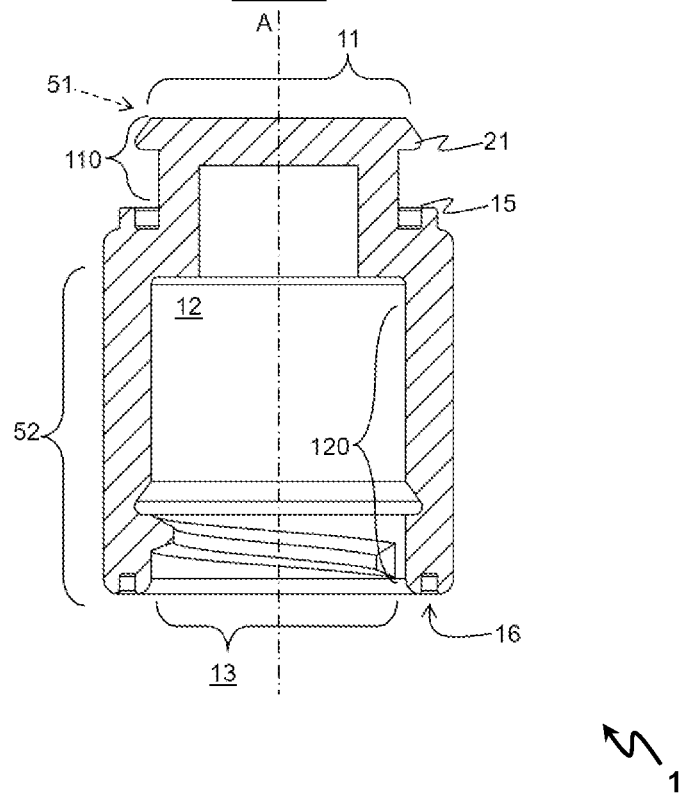
Fig.2

Fig.3a
Fig.3b
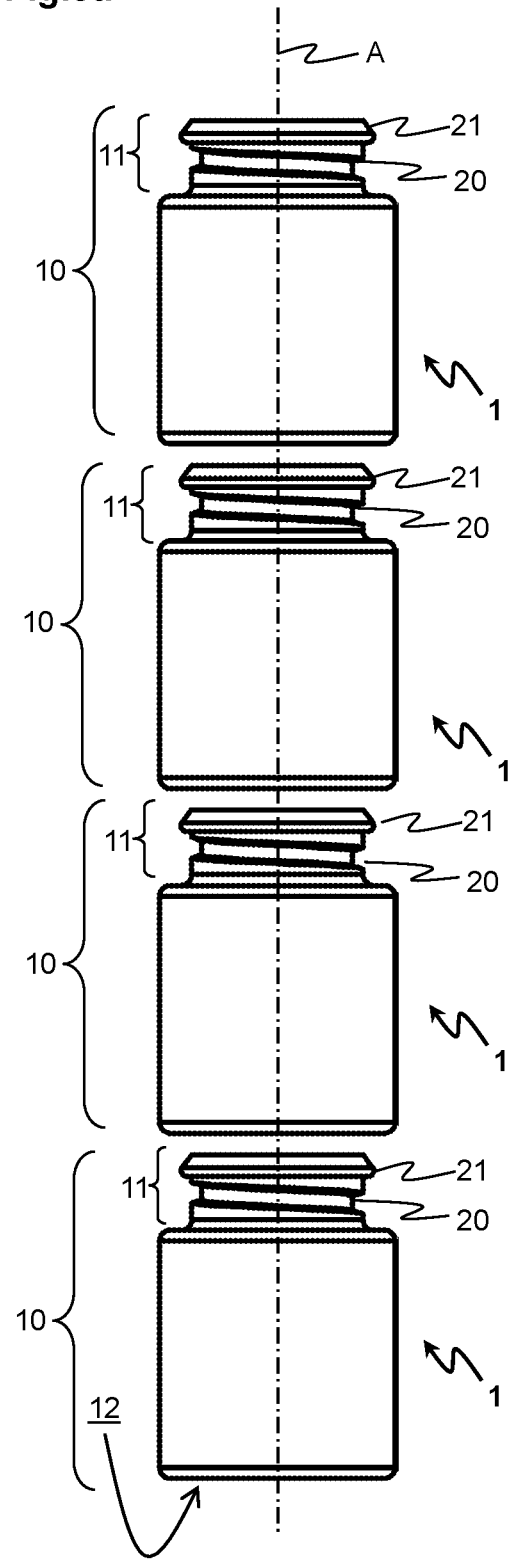
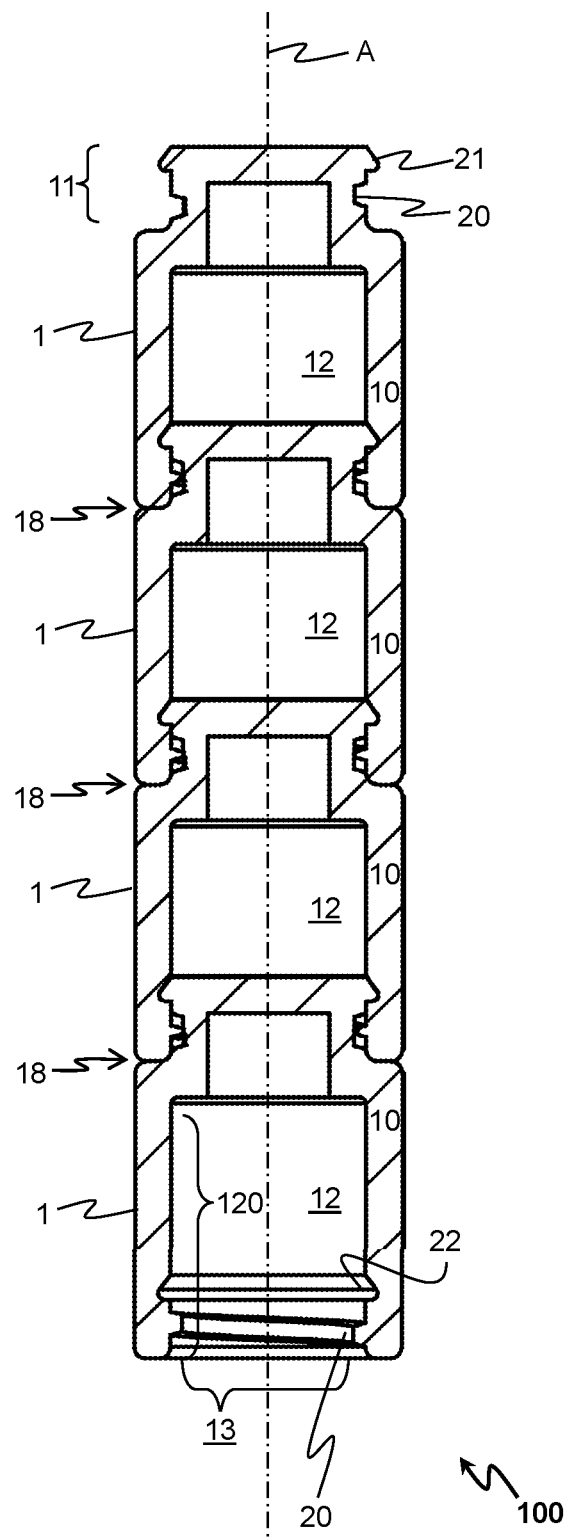

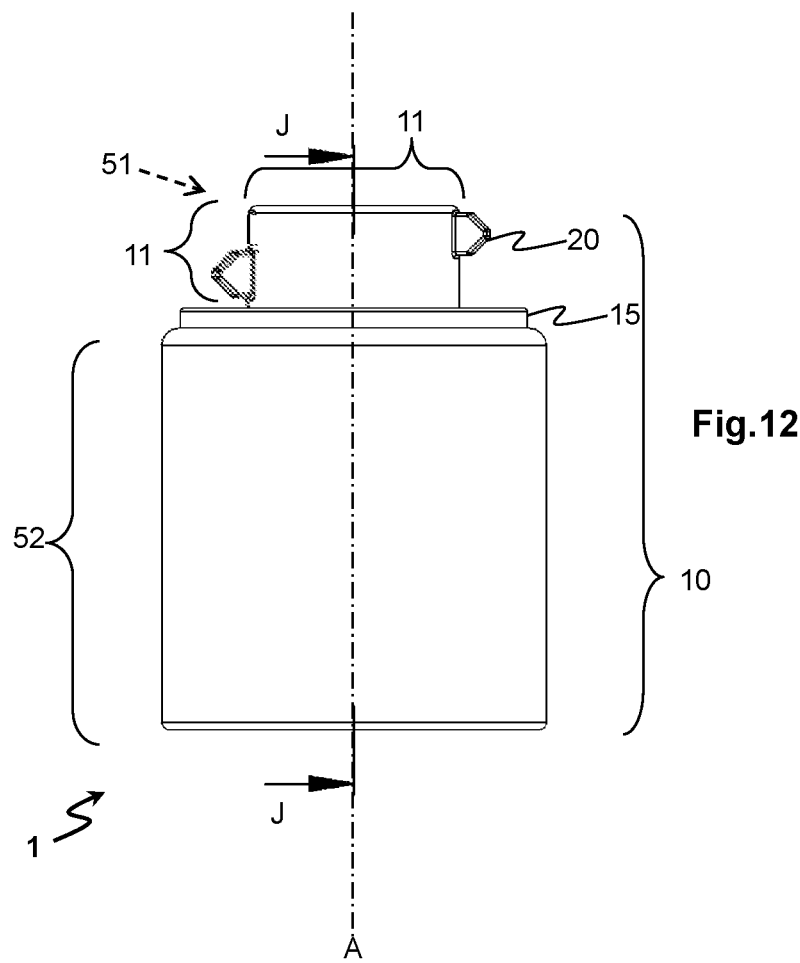
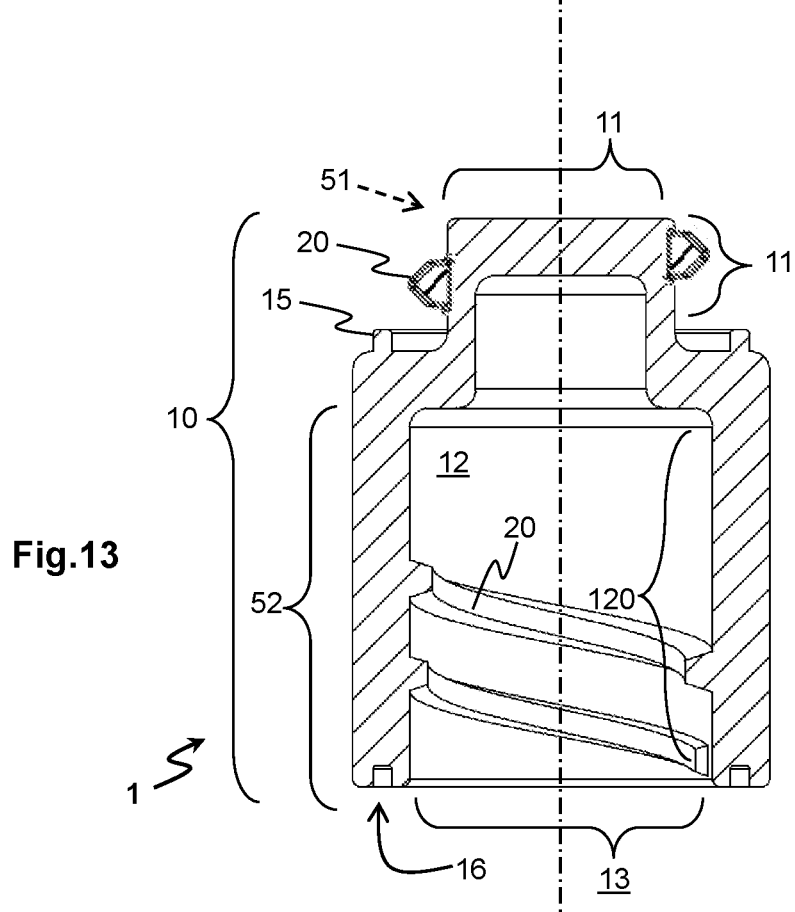

ENHANCED PEN-LIKE PORTABLE DEVICE FOR CLEANING NEEDLE-FREE IV-CONNECTORS

TECHNICAL FIELD

The present disclosure relates to an assembly of caps for protecting and cleaning needle-free intravenous connectors. In particular, the present disclosure relates to such assembly with an enhanced service life.

BACKGROUND

Protection and cleaning of needle-free intravenous connectors is provided by caps. Caps are used by removably attaching to a septum of a needle-free intravascular connector. Intravenous or intravascular connectors are abbreviated as iv-connector.

A pen-like assembly of such caps is described in EP 3 375 472 B1. For achieving the pen-like structure within the present context, a cap comprises a cavity that is accessible through an opening at an open end of the cap, and the caps further comprise a protrusion at an end that is distal to the open end. The protrusion of a first cap is introduced into the cavity of an identical, subsequent second cap, and engaged to the opening of the subsequent second cap. Thus, the cavity of the second cap is covered by the first cap.

The cavity can be provided by a flexible and adsorbent material. The flexible and adsorbent material can comprise, e.g., a synthetic foam material, or natural or synthetic fibers. Said adsorbent material can be wetted or soaked with a cleaning material in the form of liquid, for cleaning, disinfecting or sterilizing a septum of a needle-free intravascular connector. The liquid can include an alcohol, for instance, isopropanol, that is prone to transfer into gas phase by evaporation. A fluid-tight sealing can be achieved for prevention of the cleaning material from leaking. Yet, the evaporated cleaning material can leave the cavity through any gap in-between striking surfaces of two consecutive caps that are engaged to one another. The loss of cleaning material can continue until completion of the evaporation. This phenomenon results in decrease of shelf life for the caps and assembly thereof.

SUMMARY

A cap for being removably attached to a septum of a needle-free intravascular connector includes a main body. The main body includes a protrusion at a first end, a cavity, and an opening at a second end distal to the first end with regard to a main axis, for provision of access into the cavity. The cavity includes a circumferential side surface radially facing the main axis. The protrusion includes a circumferential side surface sized and shaped to geometrically match the side surface of the cavity. The main body of the cap further comprises a first material component and a second material component that are integrated with each other. The first material component has a higher hardness value in comparison with the second material component, and the main body is arranged such that the second material component is radially compressed by the first material component when the cap is engaged with a further and identical cap by an interpenetration between the protrusion and respective cavity.

An assembly of one or more caps for being removably attached to a septum of a needle-free intravascular connector. Each cap has a main body that includes a protrusion at a first end, a cavity, and an opening at a second end distal to the first end with regard to a main axis, for provision of access into the cavity. The cavity has a circumferential side surface radially facing the main axis. The protrusion has a circumferential side surface sized and shaped to geometrically match the side surface of the cavity. The main body of the one or more caps further comprises a first material component, the main body of further one or more caps comprises a second material component, and the first material component has a higher hardness value in comparison with the second material component. The one or more caps are successively arranged in an alternating fashion, such that a protrusion that is provided with the first material component is engaged with a cavity that is provided with the second material component, or a protrusion that is provided with the second material component is engaged with a cavity that is provided with the first material component.

A cap for being removably attached to a septum of a needle-free intravascular connector includes a main body. The main body includes a protrusion at a first end, a cavity, and an opening at a second end distal to the first end with regard to a main axis, for provision of access into the cavity. The cavity has a circumferential side surface radially facing the main axis. The protrusion has a circumferential side surface sized and shaped to geometrically match the side surface of the cavity. The second end of the one or more caps is provided with one or more circular ridges or grooves around the opening, that extend parallel to a main axis, and the main body is provided with one or more corresponding ridges or grooves that have respective shapes and sizes for geometrically matching and axially engaging with the ridges or grooves around the opening of an identical cap.

An assembly of one or more caps for being removably attached to a septum of a needle-free intravascular connector includes each cap having a main body. The main body includes a protrusion at a first end, a cavity, and an opening at a second end distal to the first end with regard to a main axis, for provision of access into the cavity. The cavity has a circumferential side surface radially facing the main axis. The protrusion has a circumferential side surface sized and shaped to geometrically match the side surface of the cavity. The opposing surfaces of successively arranged couples of caps are circumferentially provided with one or more adhesives or sealants around the main axis.

An assembly of one or more caps for being removably attached to a septum of a needle-free intravascular connector includes each cap having a main body. The main body has a protrusion at a first end, a cavity, and an opening at a second end distal to the first end with regard to a main axis, for provision of access into the cavity. The cavity has a circumferential side surface radially facing the main axis. The protrusion has a circumferential side surface sized and shaped to geometrically match the side surface of the cavity. One or more couples of successively arranged caps are provided with one or more removable covers that are sized and shaped for circumferentially contacting said couple of caps and covering a junction between one or more successively arranged caps.

BRIEF DESCRIPTION OF THE DRAWINGS

FIG. 1a shows an exemplary assembly of a plurality of an exemplary embodiment of the caps within the scope of the present disclosure.

FIG. 1b is an exemplary axial section view of the assembly from FIG. 1a.

FIG. 2 is an exploded axial section view depicting the successive engagement and cooperation between two identical caps (1).

FIG. 3a is an exploded side view of an assembly of a plurality of caps to be successively engaged to one another.

FIG. 3b is an axial section view of the exemplary assembly based on FIG. 3, in which the caps are successively engaged to one another.

FIG. 12 is side view of an exemplary cap according to the present disclosure.

FIG. 13 is axial section view of the cap from FIG. 12.

DETAILED DESCRIPTION

Figure 4:
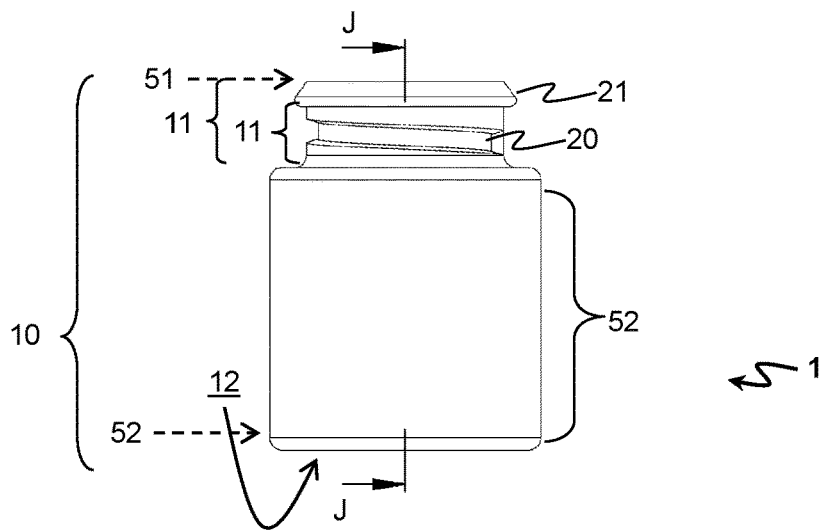
FIG. 4 shows side view of an exemplary cap within the scope of the present disclosure.

The present disclosure proposes a pen-like assembly of caps for protecting and cleaning needle-free intravenous connectors, with an enhanced service life. The present disclosure further provides a pen-like assembly of caps, with an enhanced extent of sealing in-between caps engaged to one another. The teaching in the present disclosure enhances the ease of use of the caps and assembly thereof. These are achieved by the set of features that constitute the appended claims.

The gist of the present disclosure relies on the provision of a gas-tight sealing in-between successively arranged caps that are engaged together. Any cap embodiment within the scope of the present disclosure has a main body that comprises a protrusion at a first end, a cavity, and an opening at a second end distal to the first end with regard to a main axis, for provision of access into the cavity. The cavity has a circumferential side surface radially facing the main axis. The protrusion has a circumferential side surface that is sized and shaped to geometrically match the side surface of the cavity. In any embodiment of caps, the side surface of the protrusion can include a circumferential radial extension, and the side surface of the cavity can include a corresponding circumferential radial recess geometrically matching with said extension.

Assemblies of any of the possible embodiments of caps, along with any possible combination of their features, are also proposed. Within the context of the present disclosure, the term assembly corresponds to one or more caps that are substantially identical with each other and coupled with each other.

A first approach is based on enhancing geometric compliance between striking surfaces, by contacting one or more material components that have different respective Shore hardness values. Accordingly, a first embodiment relates to one or more caps wherein:
the main body of the one or more caps comprises a first material component and a second material component that are integrated with each other, and the first material component has a higher hardness value in comparison with the second material component; and
the main body is arranged such that the second material component is radially compressed by the first material component when the cap is engaged with a further and identical cap by an interpenetration between the protrusion and respective cavity.

In a possible version of the first embodiment, the side surface of the protrusion can be provided with the first material component, and the side surface of the cavity is provided with the second material component.

The second end can be provided with the first material component for circumferentially supporting an integral layer of the second material component that is provided at the side surface of the cavity.

The side surface of the protrusion can be provided with the second material component, and the side surface of the cavity can be provided with the first material component.

The first end can be provided with the first material component circumferentially surrounded by the second material component that is provided at the side surface of the protrusion.

A difference between Shore durometer hardness values of the first material component and second material component can correspond to a value higher than 10 or within the range between 10 and 30 in terms of Shore A hardness; or to a value higher than 40 or within the range between and 60 in terms of Shore D hardness.

Within the context of the first embodiment, the present disclosure also proposes the alternating arrangement of geometrically identical caps with main bodies formed from either of the first material component and second material component. Here, the main body of the one or more caps comprises a first material component, whereas the main body of further one or more caps comprises a second material component. The first material component has a higher hardness value in comparison with the second material component. The caps are successively arranged in an alternating fashion, such that a protrusion that is provided with the first material component is engaged with a cavity that is provided with the second material component, and/or a protrusion that is provided with the second material component is engaged with a cavity that is provided with the first material component.

A second approach is based on meandering and extending a possible fluid communication route from a cavity inside a cap towards surroundings of the assembly. Accordingly, a second embodiment relates to one or more caps wherein:
- the second end of the one or more caps is provided with one or more circular ridges and/or grooves around the opening, that extend parallel to a main axis; and
- the main body is provided with one or more corresponding ridges and/or grooves that have respective shapes and sizes for geometrically matching and axially engaging with the ridges and/or grooves around the opening of an identical cap.

A third approach includes the provision of the fluid communication route with an adhesive or sealant to achieve a gas-tight sealing. Accordingly, a third embodiment relates to an assembly of caps wherein:
- opposing surfaces of successively arranged couples of caps are circumferentially provided with one or more adhesives or sealants around the main axis.

A fourth approach includes circumferentially covering junctions between caps that are engaged to one another, with one or more covers that are substantially gas impermeable. Accordingly, a third embodiment relates to an assembly of caps wherein:
- one or more couples of successively arranged caps are provided with one or more removable covers that are sized and shaped for circumferentially contacting said couple of caps and covering a junction between one or more successively arranged caps.

With reference to the appended drawings, the present disclosure proposes one or more caps (1) for being removably attached to a septum of a needle-free intravascular connector, and an assembly (100) that comprises a plurality of such caps (1) in accordance with one or more of the embodiments that are described in the present specification. FIG. 1a shows partially exploded perspective view of an exemplary assembly (100) of a plurality of exemplary caps (1) within the scope of the present disclosure. FIG. 1b is an exemplary axial section view of the assembly (100) from FIG. 1a. FIG. 2 is an exploded axial section view depicting the successive engagement and cooperation between two identical caps (1).

One or more of said caps (1) have a main body (10) that comprises the following:
- a protrusion (11) at a first end (51),
- a cavity (12)
- an opening (13) at a second end (52) distal to the first end (51) with regard to a main axis (A) of the cap (1), for provision of access into the cavity (12).

The cavity (12) has a circumferential side surface (120) that radially faces the main axis (A). The protrusion (11) has a circumferential side surface (110) with a size and shape corresponding the side surface (120) of the cavity (12); thus, arranged to geometrically fit the side surface (120) of such cavity (12) in an identical, further cap (1). When two of said caps (1) are engaged to one another, the side surface (110) of the protrusion (11) of one of the caps (1) is in mechanical contact with the side surface (120) of the cavity (12) of the other one of the caps (1). Accordingly, the side surface (110) of a protrusion (11) and the side surface (120) of the cavity (12) can be considered to serve as contact zones or, in other words, striking surfaces of a cap (1) when engaged with one or more further caps (1) to form the assembly (100).

The main body (10) of one or more caps (1) can be made of a resilient material, or one or more resilient material components. The material components can include or be selected from polymeric materials. A width of the cavity (12) can be substantially equal to or smaller than a width of the protrusion (11) perpendicular to a main axis (A); thereby achieving a radial pressure in-between striking surfaces of successively arranged caps (1) that are engaged to one another.

The one or more caps (1) can comprise a flexible and adsorbent material (14) placed into the cavity (12).

In said one or more caps (1), the size of the flexible and adsorbent material (14) can be arranged such that the fastening means (121) on the side surface (120) of the cavity (12) can be at least partly covered by the adsorbent material (14). The adsorbent material (14) can comprise one or more synthetic foam materials. Alternatively, the adsorbent material (14) can comprise one or more natural or synthetic fibers. The adsorbent material (14) can be wetted or soaked with a liquid for cleaning, disinfecting or sterilizing a septum of a needle-free intravascular connector. Such liquid is hereinafter referred to as cleaning fluid.

In a first embodiment within the scope of the present disclosure, the main body (10) of the one or more caps (1) comprises a first material component (X) and a second material component (Y) that can be provided integral to the first material component (X). In this embodiment, the first material component (X) has a higher hardness value in comparison with the second material component (Y), e.g., when measured with a Shore durometer. The main body (10) is arranged such that the second material component (Y) is radially compressed by the first material component (X) when the cap (1) is engaged with a further and identical cap (1) by an interpenetration between the protrusion (11) of one of the caps (1) and respective cavity (12) of the other one of the caps (1).

The one or more caps (1) can be arranged such that:
- the side surface (110) of the protrusion (11) is provided with the first material component (X) and the side surface (120) of the cavity (12) is provided with the second material component (Y), or
- the side surface (110) of the protrusion (11) is provided with the second material component (Y) and the side surface (120) of the cavity (12) is provided with the first material component (X).

So, when a couple of caps (1) are successively engaged to one another, a striking surface that is provided with the first material component (X) has a relatively high hardness value, when compared to a corresponding striking surface that is provided with the second material component (Y). At said engagement, mechanical forces exerted by the striking surface that is provided with the first material component (X) onto the corresponding striking surface, cause a deformation on the latter striking surface that is provided with the relatively softer second material component (Y) due to compression. This results in an adjustment with an enhanced extent of geometric fit in-between said striking surfaces.

In other words; when two consecutive caps (1) are engaged to one another, radial pressure forces are exerted onto the side surface (110) of a protrusion (11) and corresponding radial pressure forces are exerted onto the side surface (120) of the respective cavity (12). These forces result in a reversible deformation of the second material component (Y). Said deformation provides an enhancement in geometric conformity between the side surface (110) of the protrusion (11) and the side surface (120) of the cavity (12). Hence, for an evaporated portion of a cleaning fluid that may be provided inside the cavity (12), a length of an escape route (that is, flow path to be travelled for leaving the respective cap) is extended. This prolongs a duration that is required for complete evacuation of the cavity by the cleaning fluid, thereby enhancing the shelf life. Furthermore, potential gaps in-between striking side surfaces of a protrusion (11) of a cap (1) and a cavity (12) of a further, successively arranged cap (1) is minimized or eliminated. This increases a pressure drop throughout the escape route, thereby further prolonging said duration and further enhancing the shelf life.

Within the scope of the above-discussed context, a difference between respective Shore durometer hardness values of the first material component (X) and second material component (Y) can correspond to an extent of 10 or higher terms of Shore A hardness, or 40 or higher in terms of Shore D hardness. Additionally, said difference extent can be within the range between 10 and 30 in terms of Shore A hardness, or within the range between 40 and 60 in terms of Shore D hardness.

FIG. 3a is an exploded side view of an assembly (100) of a plurality of caps (1) to be successively engaged to one another. FIG. 3b is an axial section view of the exemplary assembly (100) based on FIG. 3, in which the caps (1) are successively engaged to one another.

FIG. 4 shows side view of an exemplary cap (1) within the scope of the present disclosure. Based on FIG. 3; FIG. 5a, FIG. 5b, FIG. 6a and FIG. 6b show J-J sections of exemplary possible versions of the cap (1) according to the first embodiment.

Figure 5A:
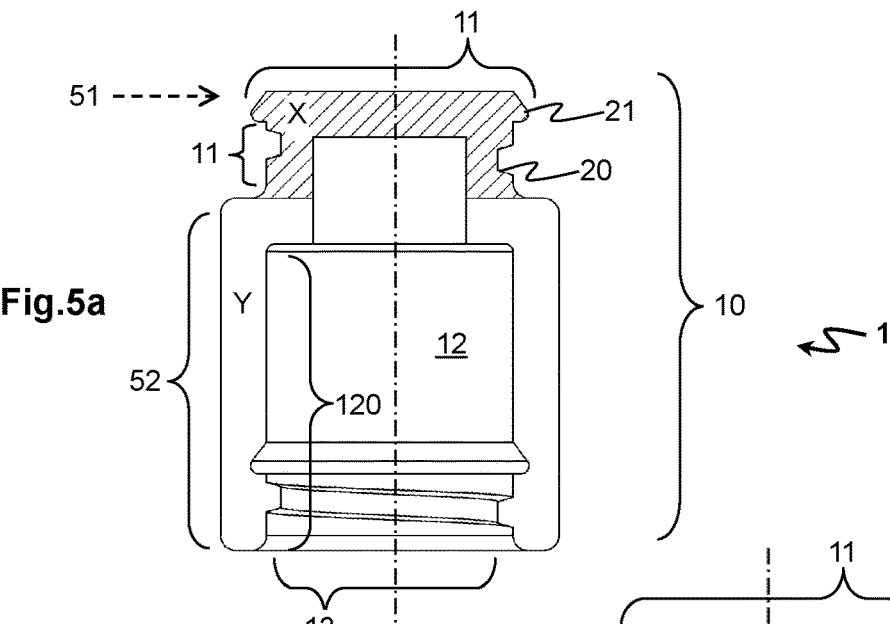
FIG. 5a shows J-J section of an exemplary possible first version of a cap according to a first embodiment, based on FIG. 4.

In a first exemplary version of the first embodiment, the side surface (110) of the protrusion (11) can be provided with the first material component (X), and the side surface (120) of the cavity (12) can be provided with the second material component (Y). FIG. 5a shows an exemplary cap (1) according to the first version of the first embodiment, wherein the shaded zones represent the first material component (X), and the non-shaded zones represent the second material component (Y). In this example, the relatively softer second end (52) that comprises the side surface (120) of the cavity (12) becomes compressed due to outwardly exerted radial forces by a relatively harder protrusion (11) of a further, identical cap (1); thereby enhancing geometric compliance between striking surfaces. The present disclosure further proposes an assembly (100) that includes a successively engaged plurality of such caps (1).

Figure 5B:
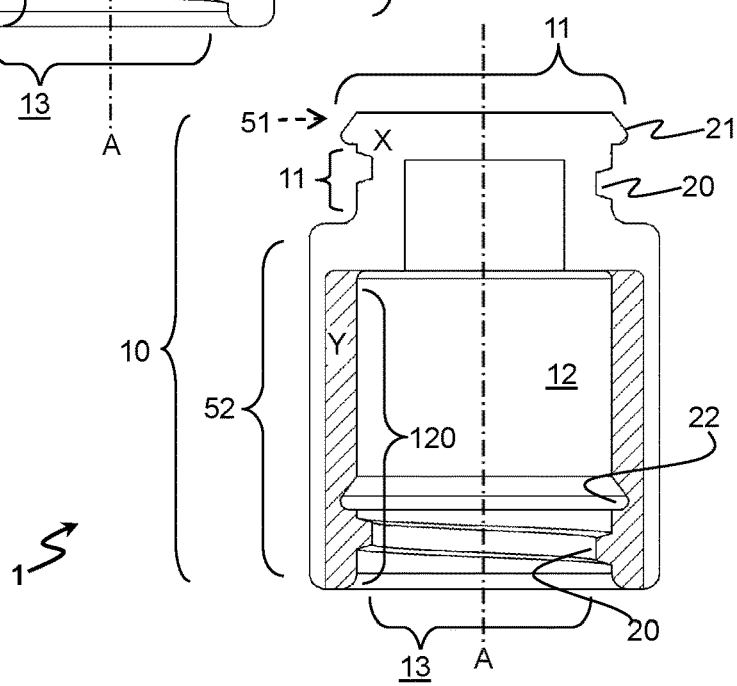
FIG. 5b shows J-J section of another exemplary possible first version of a cap according to the first embodiment, based on FIG. 4.

FIG. 5b shows an axial section of a further example according to the first version of the first embodiment, wherein the non-shaded zones represent the first material component (X) and the shaded zones represent the second material component (Y). With reference to FIG. 5b, in an example to the first version of the first embodiment,
the first end (51), or the protrusion (11), or the side surface (110) of the protrusion (11) and the second end (52) can comprise the first material component (X), and
the side surface (120) of the cavity (12) can include a circumferential layer comprising the second material component (Y).

In other words, the second end (52) can be provided with the first material component (X) for circumferentially supporting an integral layer of the second material component (Y) that is provided at the side surface (120) of the cavity (12).

In this alternative to the first version of the first embodiment, said layer provides a relatively softer, thus deformable striking surface against the side surface (110) of the protrusion (110). The first material component (X) that is provided at the second end (52) inherently surrounds said layer. Hence, the relatively softer second material component (Y) at the second end (52) can be considered as being supported against outwards radial forces by the relatively harder first material component (X). This provides an enhanced compression of the relatively softer side surface (120) of the cavity (12); thereby further enhancing the geometric compliance between cooperating striking surfaces. The present disclosure further proposes an assembly (100) that includes a successively engaged plurality of such caps (1).

In a second exemplary version of the first embodiment, the side surface (110) of the protrusion (11) can be provided with the second material component (Y), and the side surface (120) of the cavity (12) can be provided with the first material component (X). Since the side surface (120) of the cavity (12) can be intended to fit luer lock geometry, the geometric shape retention thereof can be considered advantageous. A long-term compression of the second material component (Y) by the relatively harder first material component (X) can potentially result in a permanent deformation of the side surface (120) of the cavity (12). Since the geometry of protrusion (11) is no longer important when in use upon disengagement from a respective cavity (12) of a further cap (1), it can be considered advantageous in an aspect, to arrange the relatively compressible second material component (Y) at the side surface (110) of the protrusion (11), rather than at the side surface (120) of the cavity (12).

Figure 6A:
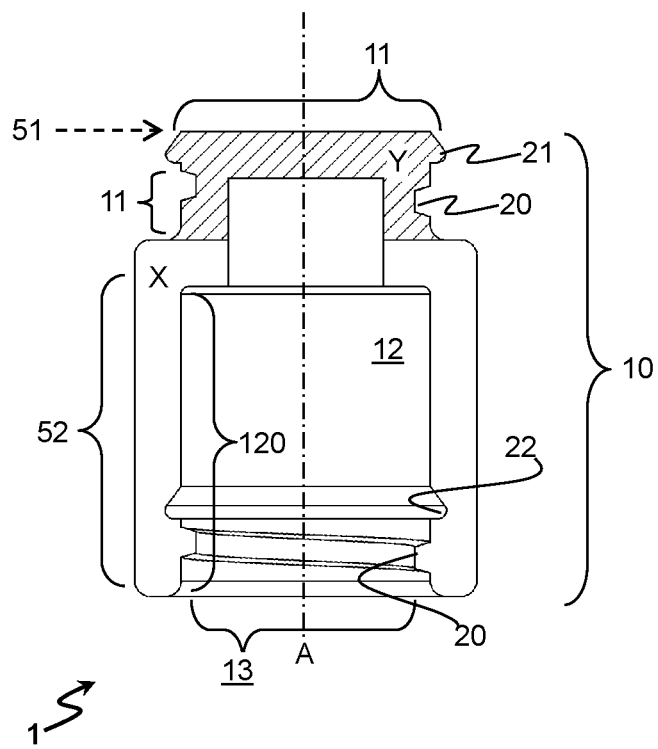
FIG. 6a shows J-J section of an exemplary possible second version of a cap according to the first embodiment, based on FIG. 4.

For instance, the first end (51) or the protrusion (11) can be provided with the second material component (Y), and the second end (52) can be provided with the first material component (X). For instance, the first end (51) or the protrusion (11) can be formed from the second material component (Y), and the second end (52) can be formed from the first material component (X). FIG. 6a shows an example according to the second version of the first embodiment, wherein non-shaded zones represent the first material component (X), and shaded zones represent the second material component (Y). In this example, the relatively softer first end (51) that comprises the side surface (110) of the protrusion (11) can become compressed due to inwardly exerted radial forces by a relatively harder side surface (120) of a cavity (12) of a further, identical cap (1); thereby enhancing geometric compliance between striking surfaces. The present disclosure further proposes an assembly (100) that includes a successively engaged plurality of such caps (1).

Figure 6B:
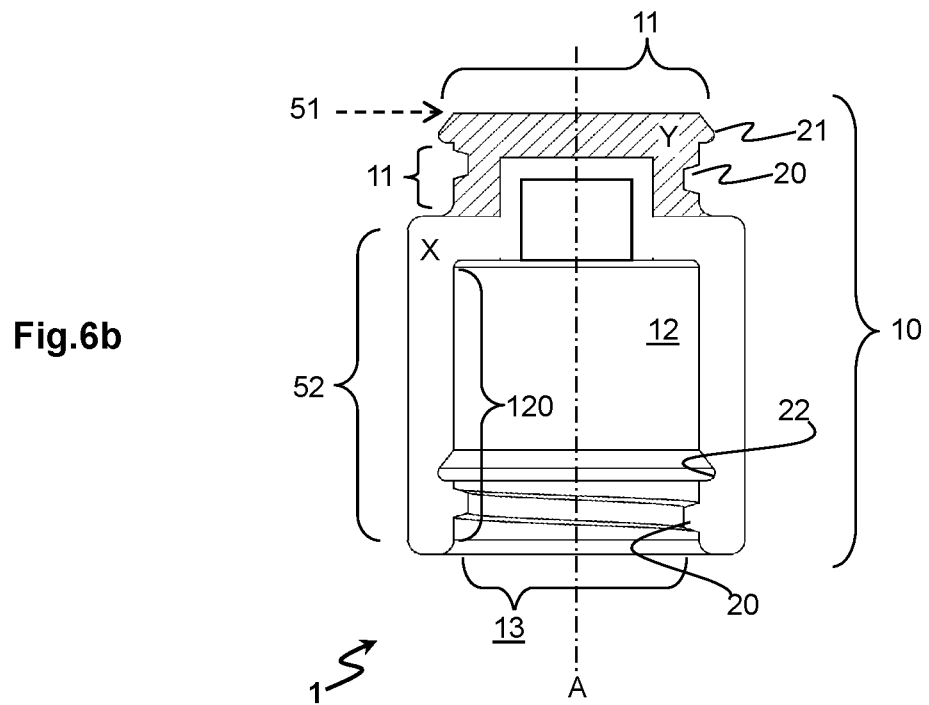
FIG. 6b shows J-J section of another exemplary possible second version of a cap according to the first embodiment, based on FIG. 4.

FIG. 6b shows an axial section of a further example according to the second version of the first embodiment, wherein the non-shaded zones represent the first material component (X) and the shaded zones represent the second material component (Y). With reference to FIG. 6b, in an example to the second version of the first embodiment,
the second end (52), or the cavity (12), or the side (120) surface of the cavity (12) and the first end (51) can comprise the first material component (X), and
the first end (51), or the protrusion (11), or the side surface (110) of the protrusion (11) can include an integral outer layer formed from the second material component (Y).

In other words, the first end (51) can be provided with the first material component (X) circumferentially surrounded by the second material component (Y) that is provided at the side surface (110) of the protrusion (11).

In this alternative to the second version of the first embodiment, the layer that is formed from the second material component provides a relatively softer, thus deformable striking surface against the side surface (120) of a cavity (12) in an identical further cap (1). The first material component (X) that is provided at the first end (51) is inherently surrounded by said layer. Hence, the relatively softer second material component (Y) at the first end (51) can be considered as being supported against inwards radial forces by the relatively harder first material component (X). This provides an enhanced compression of the relatively softer side surface (110) of the protrusion (11); thereby further enhancing the geometric compliance between cooperating striking surfaces. The present disclosure further proposes an assembly (100) that includes a plurality of such caps (1) engaged to each other.

Figure 7:
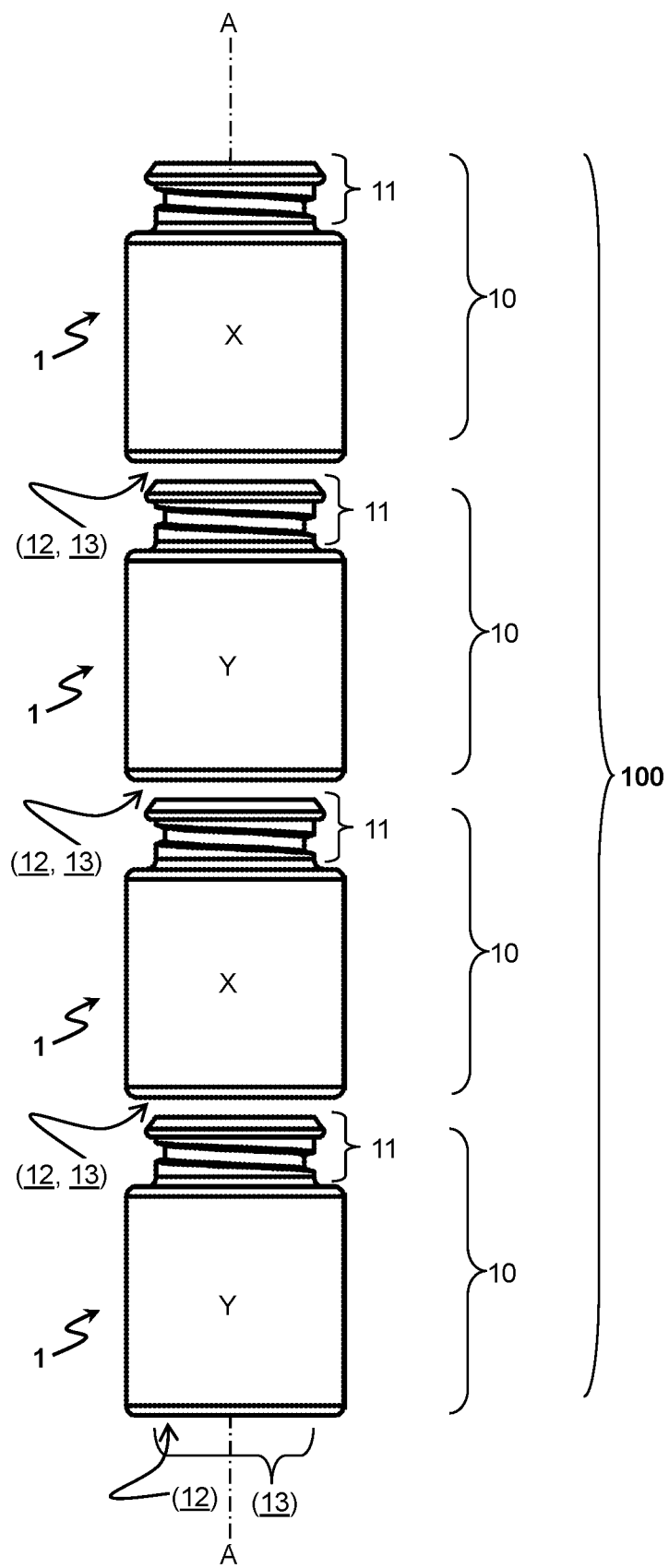
FIG. 7 shows an exploded side view of an exemplary assembly of caps according to a third version of the first embodiment.

FIG. 7 shows an exploded side view of an exemplary assembly (100) of caps (1) according to a third version of the first embodiment, in which one or more caps (1) that have a main body (10) comprising (e.g., formed from) the first material component (X) is arranged in an alternating fashion with one or more further caps (1) that have a main body (10) comprising (e.g., formed from) the second material.

With reference to FIG. 7, in the third version of the first embodiment; one or more of the caps (1) can comprise a main body (10) that is formed from the first material component (X), and further one or more of the caps (1) can comprise a main body (10) that is formed from the second material component (Y). With the third version of the first embodiment, an assembly (100) can be formed by alternating arrangement of successive caps in terms of material components that form respective main bodies (10).

In other words, the one or more caps (1) that comprise the main body (10) formed from the first material component (X) can be engaged to one or more respective further caps (1) that comprise a main body (10) formed from the second material component (Y). Upon obtainment of an assembly (100) of one or more caps (1) in such alternating fashion in terms of material components, that differ from each other in hardness:

the side surface (110) of the protrusion (11) of one or more caps (1) comprising a main body (10) formed from the first material component (X) is engaged with the side surface (120) of the cavity (12) of one or more corresponding further caps (1) comprising a main body (10) formed from the second material component (Y); and/or the side surface (110) of the protrusion (11) of one or more caps (1) comprising a main body (10) formed from the second material component (Y) is engaged with the side surface (120) of the cavity (12) of one or more corresponding further caps (1) comprising a main body (10) formed from the first material component (X).

An assembly (100) of caps (1) according to the third embodiment can be also described as follows:

the main body (10) of the one or more caps (1) comprises a first material component (X), the main body (10) of further one or more caps (1) comprises a second material component (Y), and the first material component (X) has a higher hardness value in comparison with the second material component (Y), the caps (1) are successively arranged in an alternating fashion, such that a protrusion (11) that is provided with the first material component (X) is engaged with a cavity (12) that is provided with the second material component (Y), and/or a protrusion (11) that is provided with the second material component (X) is engaged with a cavity (12) that is provided with the first material component (Y).

Due to the alternating arrangement of the first material component (X) and second material component (Y), the hardness difference between corresponding striking surfaces in one or more caps (1) that are engaged with one another results in that: the relatively harder one of the first and second material components compresses the corresponding striking surface that has a relatively lower value of hardness. Thus, the tightness in-between striking surfaces is increased, that is, local flow area is decreased throughout the escape route, or even eliminated. This increases the pressure drop that applies to the vapor of the cleaning fluid, thereby retards or stops the loss of cleaning fluid. Thus, the shelf-life is enhanced.

In a further approach within the scope of the present disclosure, the above-mentioned pressure drop can also be increased by extending a length of the escape route by formation of meanders thereon. According to this concept:

the second end (52) of the one or more caps (1) can be provided with one or more circular ridges (15) and/or grooves (16) around the opening (13), that extend parallel to a main axis (A), and the main body (10) can be provided with one or more corresponding ridges (15) and/or grooves (16) that have respective shapes and sizes for axially engaging with the ridges (15) and/or grooves (16) around the opening (13) of an identical cap (1).

Figure 8:
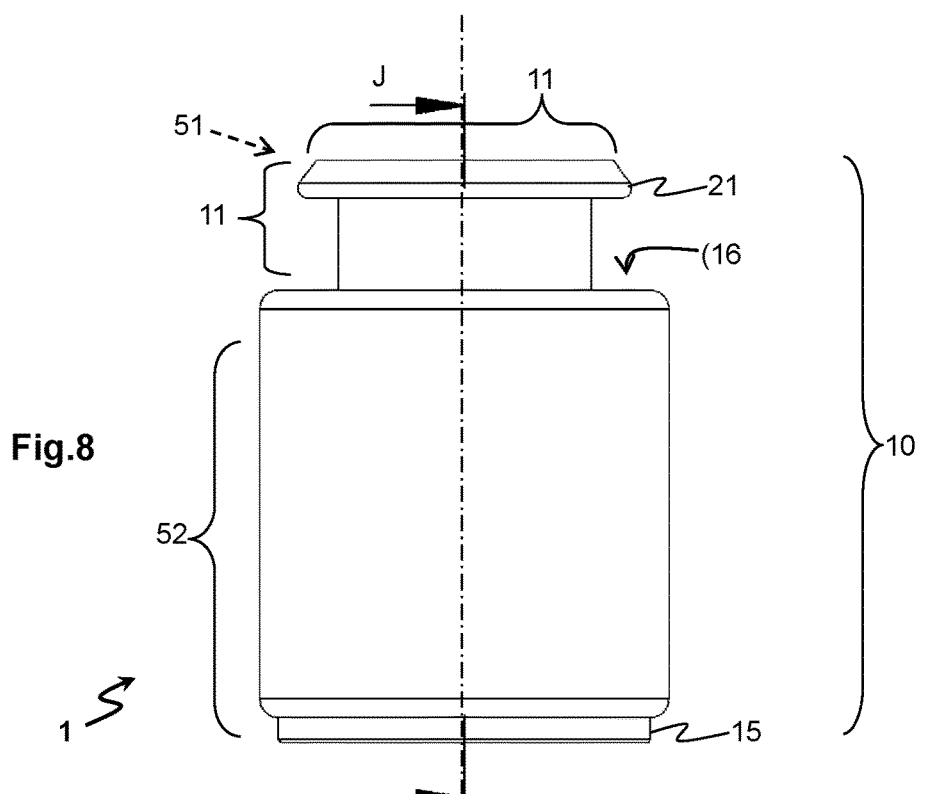
FIG. 8 is side view of an exemplary first version of cap according to a second embodiment.
Figure 9:
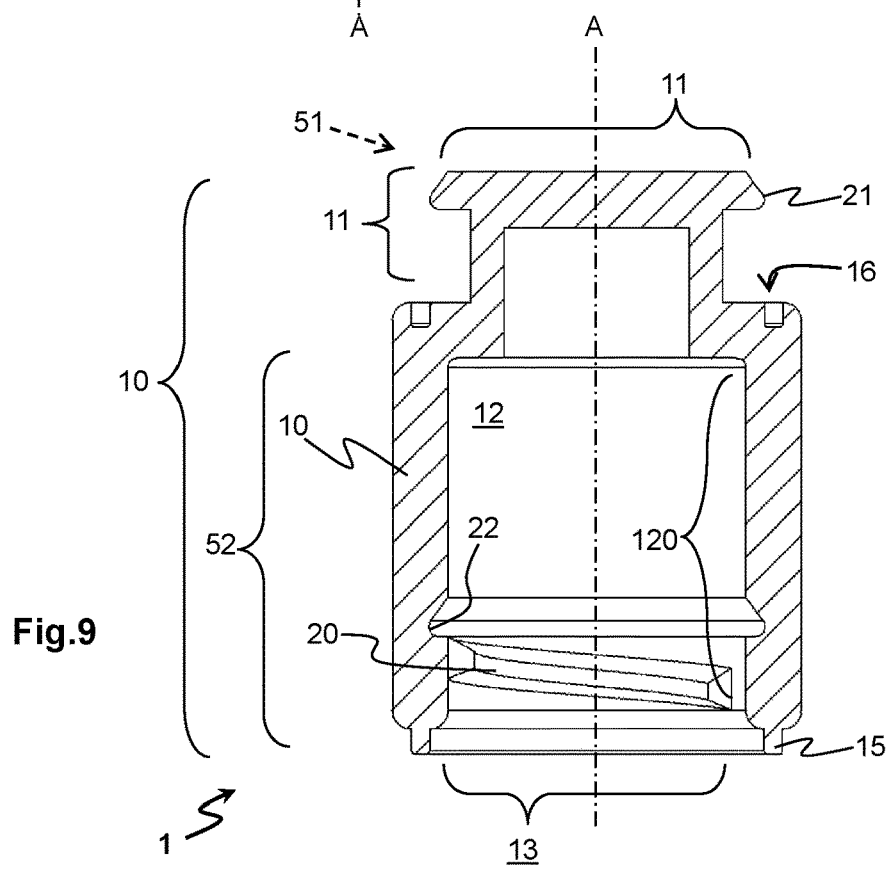
FIG. 9 shows an axial section of the cap from FIG. 8.

FIG. 8 is side view of an exemplary first version of cap (1) according to a second embodiment. FIG. 9 shows an axial section of the cap (1) from FIG. 8. In the cap (1) shown in FIG. 9, the second end (52) is provided with one or more ridges (15) (here: one), and the main body (10) is provided with one or more corresponding grooves (16) (here: one) for axially engaging, geometrically matching and thus cooperating with respective one or more ridges (20) of an identical cap (1).

Figure 10:
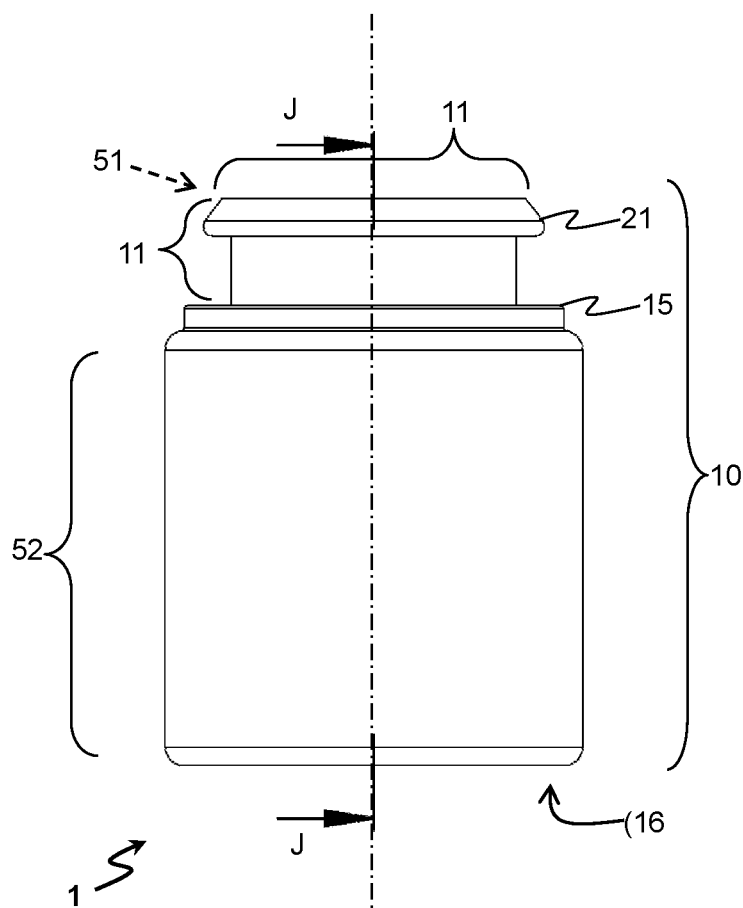
FIG. 10 is side view of an exemplary second version of cap according to the second embodiment.
Figure 11:
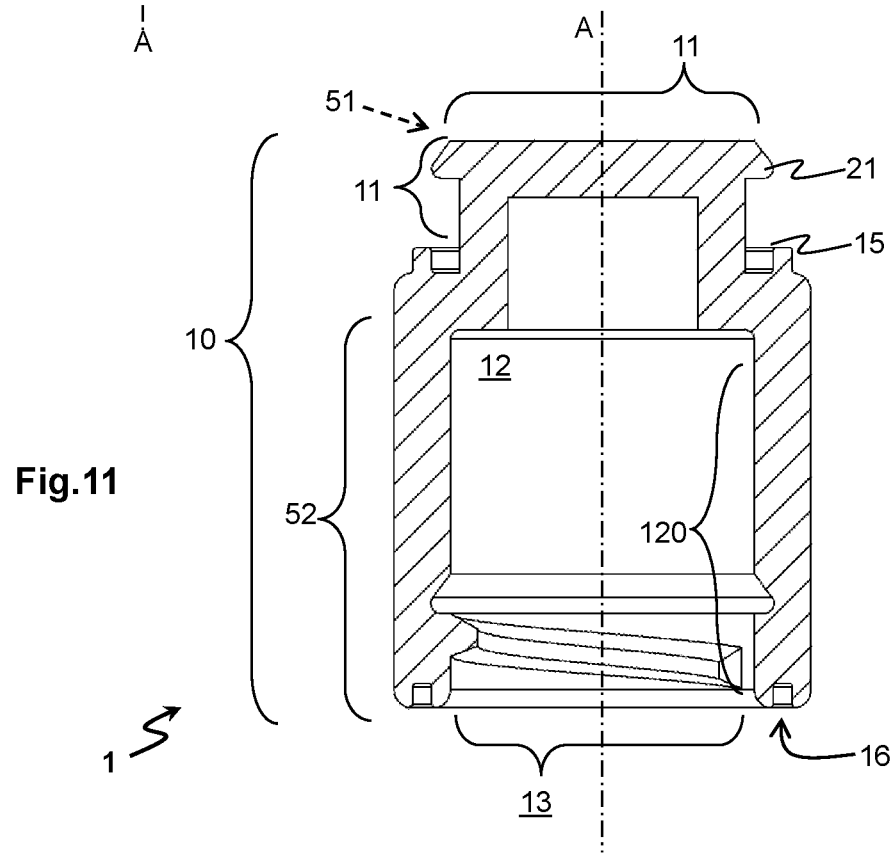
FIG. 11 shows an axial section of the cap from FIG. 10.

Alternatively, or additionally, the second end (52) can be provided with one or more grooves (16), and the main body (10) can be provided with one or more corresponding ridges (15) for matching and cooperating with respective one or more grooves (16) of an identical cap (1). FIG. 10 is side view of such exemplary second version of cap (1) according to the second embodiment. FIG. 11 shows an axial section of the cap (1) from FIG. 10. In the cap (1) shown in FIG. 11, the second end (52) is provided with one or more grooves (16) (here: one), and the main body (10) is provided with one or more corresponding ridges (15) (here: one) for matching and cooperating with respective grooves (16) of an identical cap (1).

A vapor of a cleaning fluid that can be provided inside the cavity (12) can emerge due to partial evaporation of the cleaning fluid. The vapor is expected to be prone to leak from the cavity (12) radially relative to the main axis (A), through any gap remaining in-between striking surfaces of successively engaged caps (1). Upon engaging a plurality of caps (1) according to the second embodiment, the ridges (15) and/or grooves (16) around the opening (13) interpenetrate and match with respective grooves (16) and/or ridges (20) that have corresponding shapes and sizes for axially engaging or matching with said ridges (15) and/or grooves (16) around the opening (13). This feature results in formation of a meandering transverse to the radial direction regarding the main axis (A), thereby extending the escape route of a vapor of a cleaning fluid provided in the cavity (12). Hence, the vapor is subjected to an enhanced extent of pressure drop along the escape route; and the tendency of the vapor of cleaning fluid to leave the cavity is minimized or eliminated. As a result, this approach also or further enhances the shelf life when taken alone or in combination with the features in any version of the first embodiment.

In any embodiment or version of cap (1) that is discussed in the present specification, the side surface (110) of the protrusion (11) and the side surface (120) of the cavity (12) can have pre-formed conjugate reversible fluid-tight fastening means, such that the cavity (12) is hermetically sealable by introduction and fastening of an identical protrusion (11) of a further cap (1) thereinto. The conjugate fastening means can be an extension (21) around one of the side surfaces (110 or 120) and a corresponding recess (22) around the respective, complementary side surface (120 or 110). In such cap (1), the conjugate fastening means are thus arranged to enable a reversible snap-fit connection between the fastening means on the side surface (120) of the cavity (12) and that on the side surface (110) of an identical protrusion (11) of a further cap (1). Alternatively, the conjugate fastening means can be in the form of screw threads (20).

FIG. 12 is side view of an exemplary cap (1) according to the present disclosure. FIG. 13 is axial section view of the cap (1) from FIG. 12. In this exemplary cap (1), the side surface (120) of the cavity (12) is provided with screw threads that can be sized and shaped in accordance with medical standards for luer locks (e.g., Luer taper fitting, standards of which being currently governed by ISO 80369); and the side surface (110) of the protrusion (11) is provided with corresponding screw threads to cooperate with those on the side surface (120) of the cavity (12) of a further, identical cap. Such cap (1) can be in accordance with any of the versions of any of the embodiments that are discussed in the present specification. The exemplary cap (1) shown in FIG. 12 and FIG. 13 is in accordance with the second embodiment.

As shown in the drawings other than FIG. 12 and FIG. 13, the side surface (110) of the protrusion (11) can include a circumferential radial extension (21), and the side surface (120) of the cavity (12) can include a corresponding circumferential radial recess (22) geometrically matching with said extension (21). This feature further extends the length of the escape route, causes a further pressure drop along the escape route, thereby further minimizing the loss of any cleaning fluid that can be evaporated in the cavity (12). Thus, the shelf life of the caps (1) and an assembly thereof (100) is further enhanced. Additionally, this feature provides a snap-fit mechanical communication between successively engaged caps (1), thereby enhancing mechanical stability of the assembly (100) against radial forces exerted thereon.

Figure 14:
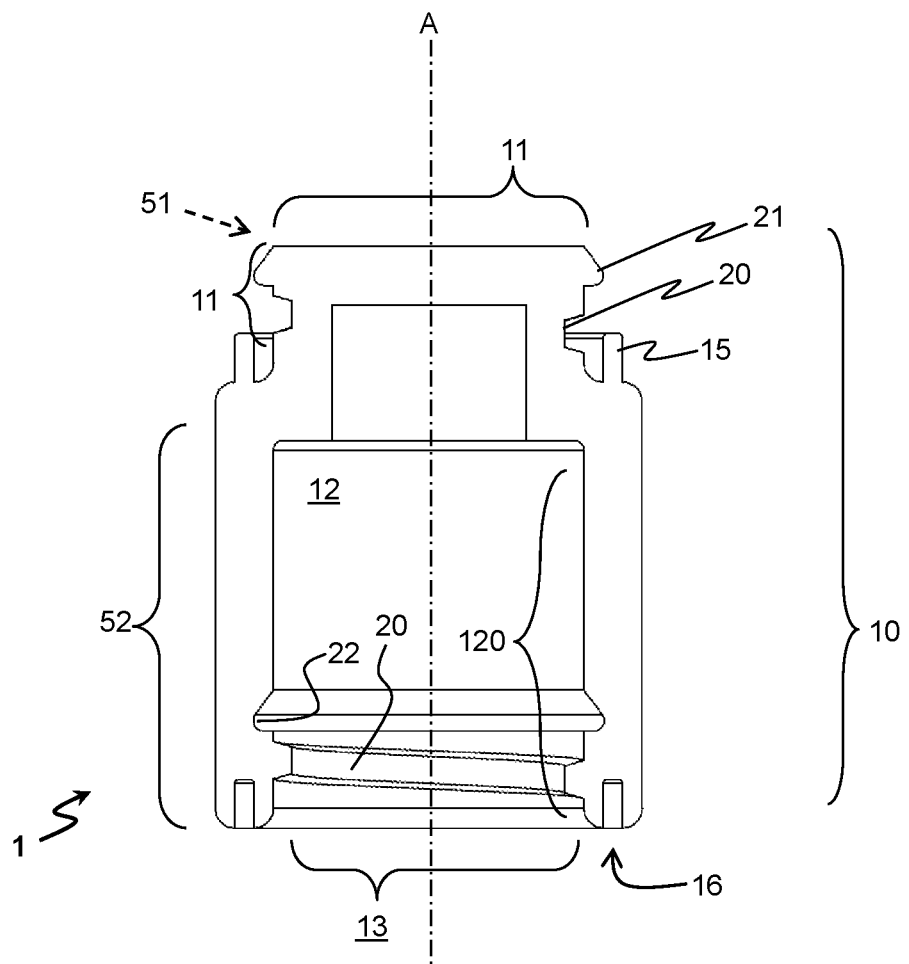
FIG. 14 is axial section view of an exemplary cap which is provided with screw threads, extension, recess, one or more ridges and one or more grooves.
Figure 15:
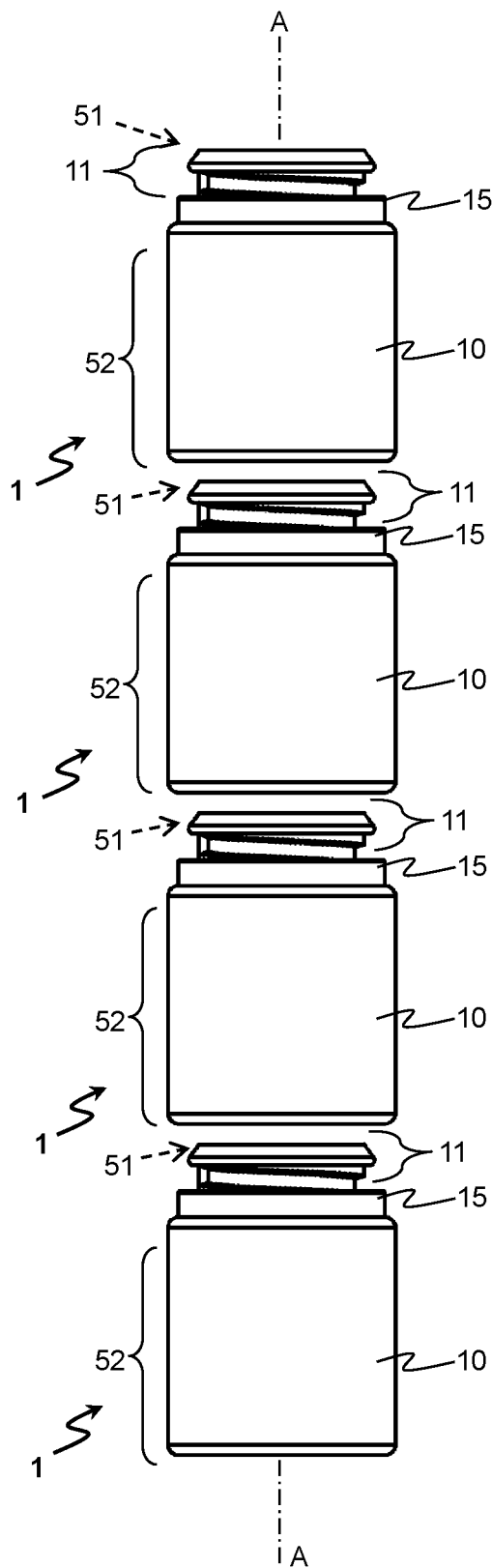
FIG. 15 shows an exploded side view of an assembly that can be formed from a plurality of caps from FIG. 14.
Figure 16:
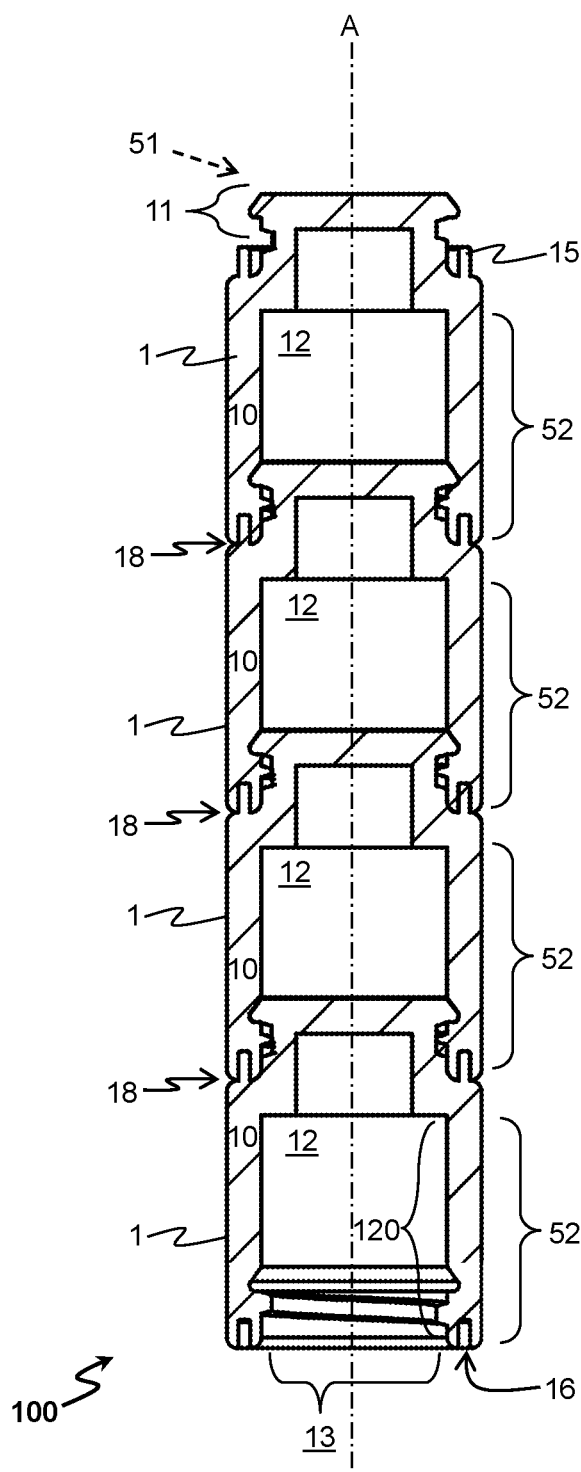
FIG. 16 is axial section view of the assembly from FIG. 15.

FIG. 14 shows axial section of an exemplary cap (1) which is provided with screw threads, extension (21), recess (22), one or more ridges (15) and one or more grooves (16). As exemplified here, features of several embodiments or different versions that are discussed within the present specification can be combined with each other. That is, a cap (1) or an assembly (100) thereof can be in accordance with multiple embodiments or versions that are discussed in the present disclosure, thus being within the scope of the present disclosure. To address this fact with an example, FIG. 15 shows an exploded side view of an assembly (100) that can be formed from a plurality of caps (1) from FIG. 14. FIG. 16 is axial section of the assembly (100) from FIG. 15. FIG. 16 visualizes mechanical engagement between the following:

- screw threads on the side surface (110) of the protrusion (11) of a first cap (1) and corresponding screw threads on the side surface (120) of the cavity (12) of a successively arranged further cap (1);
- ridge(s) (15) on a first cap (1) and corresponding groove(s) (16) on a successively arranged further cap (1)
- extension(s) (21) on a first cap (1) and corresponding recess(es) (22) on a successively arranged further cap (1).

Figure 17:
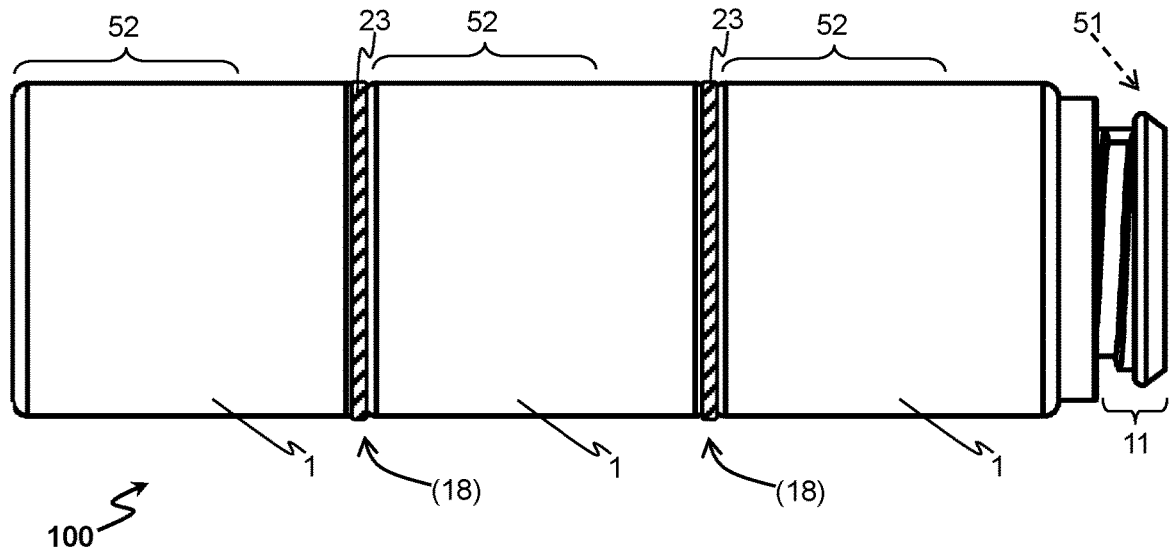
FIG. 17 schematically represents side view of an assembly according to a third embodiment.

In an exemplary third embodiment, the opposing surfaces (e.g., striking surfaces) of one or more successively arranged couples of caps (1) can be circumferentially provided with one or more adhesives or sealants (23) around the main axis (A). The adhesive or sealant (23) can be considered as provided at a junction (18) between one or more couples of caps (1) that are engaged to each other. FIG. 17 schematically represents side view of an assembly (100) according to the third embodiment, wherein the adhesive or sealant (23) is emphasized with shaded zones. Loci of junctions (18) that can be overlapped by respective loci of adhesive or sealant are indicated in FIG. 17. Yet, the positioning or amount of the adhesive or sealant (23) can be arranged such that the adhesive or sealant (23) can be exposed to visual observation upon disengaging a couple of successively engaged caps (1). The one or more adhesives ore sealants (23) can provide a gas-tight sealing, for instance, upon curing thereof.

The adhesive or sealant (23) can be considered to be arranged for being torn when disengaging a respective couple of caps (1). The adhesive or sealant (23) can be further considered as a gas-tight threadlocker, and can be in liquid form at disclosure onto one or more of said opposing surfaces, to be cured after engagement of said successively arranged couple of caps (1). Due to that the adhesive or sealant (23) is circumferentially applied, the escape route of the vapor of the cleaning fluid is sealed in radial directions, hence the vapor of the cleaning fluid is restrained inside the cavity (12) until the time when a respective cap (1) is disengaged for use. As a result, the shelve life is enhanced.

When an assembly (100) is formed from successively arranged one or more couples of caps (1) that are engaged to one another, it shall be considered that the protrusion (11) of one or more caps (1) is received by a cavity (12) of a respective cap (1). So, it can be considered that the first end (51) of such cap (1) is substantially hidden when engaged with a further cap (1), but outer side surfaces the second end (52) are exposed for visual observation from outside. Second end (52) of the one or more caps (1) can have a cylindrical outer geometry, such that, after introduction of the protrusion (11) of the cap (1) into a respective cavity (12), the second end (52) that remains exposed corresponds to a cylinder side surface. Thus, an assembly (100) of such caps (1) can be considered to have a substantially cylindrical outer side surface around the main axis (A). The cylindrical outer side surfaces of the second ends (52) of successively engaged caps (1), and inherently a circumferential junction (18) therebetween, can be provided with a cover (17) that is circumferentially in contact with said outer side surfaces for prevention of mass (here: vapor of the cleaning fluid) transfer from one or more cavities (12) to surroundings.

Figure 18:
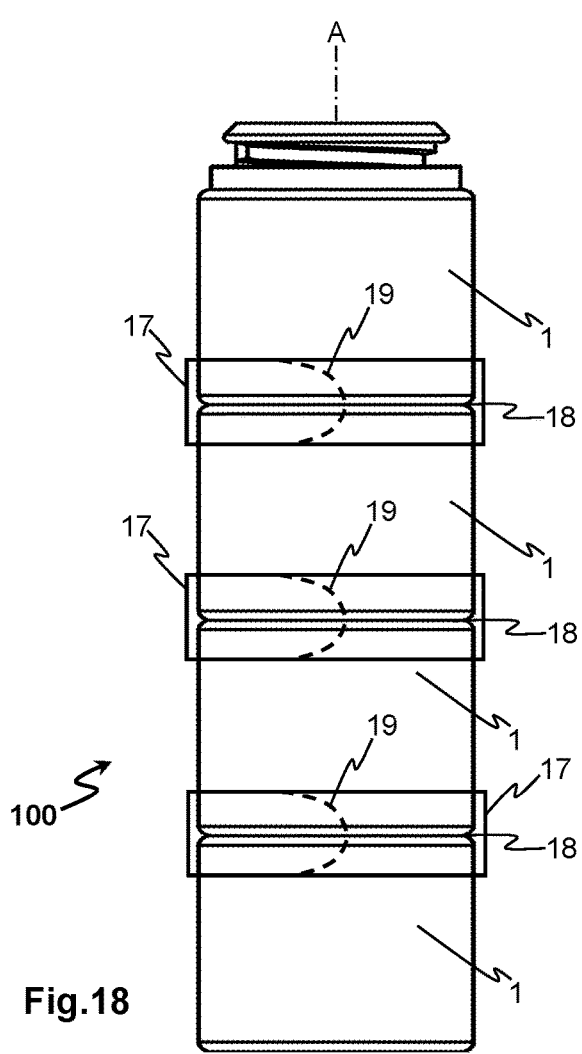
FIG. 18 shows side view of an assembly according to an exemplary first version of a fourth embodiment, that includes one or more covers.
Figure 19:
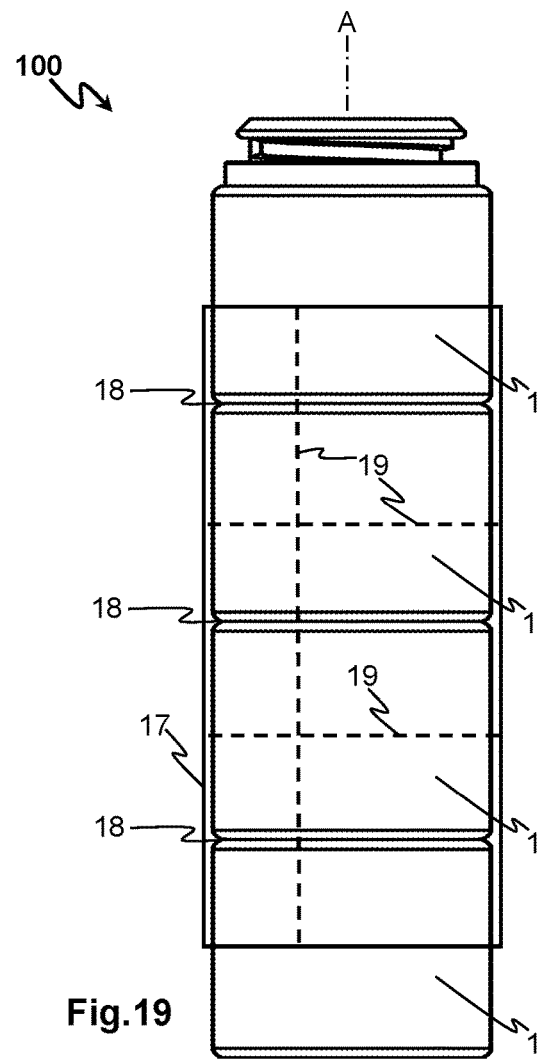
FIG. 19 shows side view of an assembly according to an exemplary second version of a fourth embodiment, that includes one or more covers.

FIG. 18 and FIG. 19 respectively show side views of assemblies (100) according to exemplary first and second versions of a fourth embodiment. In the fourth embodiment, one or more couples of successively arranged caps (1) can be provided with one or more removable covers (17) that are sized and shaped for circumferentially contacting said couple of caps (1) and covering a junction (18) between said couple of caps (1). In this embodiment, the escape route is blocked from outside of the assembly (100). The one or more covers (17) thus obstruct the escape route of the vapor of the cleaning liquid that might reach to the junction (18) through a possible gap in-between the striking surfaces of caps (1) engaged to one another. As a result, the cleaning liquid and its vapor are restrained inside the cavity (12), and the shelf life is extended.

With reference to FIG. 18, the one or more covers (17) can be in the form of removable belts, each having a size and shape for circumferentially covering a respective junction (18) between two caps (1) that are engaged to one another. Simply removing a belt-shaped cover (17) exposes a respective junction (18), thereby allowing the disengagement of a single cap (1). The one or more covers (17) can be provided with one or more series of perforations (19), thereby facilitating the removal of the covers (17) by tearing manually.

With reference to FIG. 19, the one or more covers (17) can be sized and shaped for circumferentially contacting a plurality of couples of caps (1) and for covering one or more (e.g., a respective plurality of) junctions (18) between said plurality of couples of caps (1). Such cover (17) can be provided with one or more circumferential series of perforations (19) around the main axis (A), arranged in-between successively arranged junctions (18). Such series of perforations (19) allow partial removal of the cover (17), for instance by manual tearing, to expose a single junction (18) for disengagement of a single, respective cap (1).

In a possible version of the fourth embodiment, an inner surface of the cover (17) that faces the caps (1) can be provided with an adhesive layer (not shown) for removably adhering the cover (17) to the couple of caps (1).

In any version of the fourth embodiment, the cover (17) can be formed from a sheet material, for instance, from a gas-impermeable flexible film that can be employed in medical or food industries. The cover (17) can be arranged to exert radial pressure force onto the caps (1) towards the main axis (A), by being formed from a resilient material such as an elastomer, or from a heat-shrinkable material that is subjected to heat-shrinking upon placement around an assembly (100) of successively engaged one or more caps (1).

In the one or more caps (1), the protrusion (11) can have a rounded edge distal to the cavity (12). This feature facilitates an intentional disengagement of an endmost one of caps (1) in an assembly (100), by manual exertion of a radial force onto said cap (1) relative to one or more further caps (1) in said assembly (100).

Any version of the assembly (100) of a plurality of caps (1) can be further provided with a clip (30) for attachment of the assembly (100) to a pocket on a garment. The clip (30) can be arranged to be rotatable relative to the assembly (100); for instance, around a radial direction with regard to the main axis (A), as a rotation axis. The clip (30) can comprise an attachment means (31) for engaging with a hook. For instance, the attachment means (31) can be in the form of a hole as shown in FIG. 1a and FIG. 1b, or in the form of a hook. The attachment means (31) enables that the assembly (100) can be hung at the clip (30) to a hook of an e.g., serum hanger, or an iv pole, or an iv holder that can be used in therapeutic facilities.

The assembly (100) or a clip (30) of the assembly (100) can comprise an axially slidable holder (32) for circumferentially covering and supporting a junction (18) in-between a couple of caps (1) that are engaged to one another. The holder (32) can have a width (W) of 0.5 centimeters or greater, for mechanically supporting the couple of caps (1) against disengaging due to bending by a radial force manually exerted onto a further cap (1) in the assembly.

By being slidable on the assembly (100) parallel to the main axis (A), the holder (32) can be moved one cap (1) further at disengaging of a cap (1); wherein a successive, next junction (18) is circumferentially covered and mechanically supported in radial directions. As a result, at intentionally disengagement of a foremost cap (1) by manual exertion of a radial force thereonto, an unintentional disengagement of a further cap (1) can be easily prevented.

REFERENCE SIGNS 1 cap
10 main body
11 protrusion
110 side surface (of the protrusion)
111 fastening means (on the side surface of the protrusion)
12 cavity
120 side surface (of the cavity)
121 fastening means (on the side surface of the cavity)
13 opening
14 adsorbent material
15 ridge
16 groove
17 cover
18 junction
19 perforation
20 screw thread
21 extension
22 recess
23 adhesive or sealant
30 clip
31 attachment means
32 holder
51 first end
52 second end
100 assembly
A main axis
W width
X first material component
Y second material component

The invention claimed is:

1. A cap for being removably attached to a septum of a needle-free intravascular connector, comprising:
a main body comprising:
a protrusion at a first end;
a cavity; and
an opening at a second end distal to the first end with regard to a main axis, for provision of access into the cavity,
the cavity having a circumferential side surface radially facing the main axis,
the protrusion having a circumferential side surface sized and shaped to geometrically match the side surface of the cavity, wherein:
the main body of the cap further comprises a first material component and a second material component that are integrated with each other, and the first material component has a higher hardness value in comparison with the second material component, and
the main body is arranged such that the second material component is radially compressed by the first material component when the cap is engaged with a further and identical cap by an interpenetration between the protrusion and respective cavity.

2. The cap according to claim 1, wherein the side surface of the protrusion is provided with the first material component, and the side surface of the cavity is provided with the second material component.

3. The cap according to claim 2, wherein the second end is provided with the first material component for circumferentially supporting an integral layer of the second material component that is provided at the side surface of the cavity.

4. The cap according to claim 1, wherein the side surface of the protrusion is provided with the second material component, and the side surface of the cavity is provided with the first material component.

5. The cap according to claim 4, wherein the first end is provided with the first material component circumferentially surrounded by the second material component that is provided at the side surface of the protrusion.

6. The cap according to claim 1, wherein a difference between Shore durometer hardness values of the first material component and second material component corresponds to a value within the range between 10 and 30 in terms of Shore A hardness, or to a value within the range between 40 and 60 in terms of Shore D hardness.

7. The cap according to claim 1, wherein the side surface of the protrusion includes a circumferential radial extension, and the side surface of the cavity includes a corresponding circumferential radial recess geometrically matching with said extension.

8. An assembly comprising one or more of the caps according to claim 1.

9. An assembly of one or more caps for being removably attached to a septum of a needle-free intravascular connector, each cap having a main body that comprises:
   a protrusion at a first end,
   a cavity, and
   an opening at a second end distal to the first end with regard to a main axis, for provision of access into the cavity,
   the cavity having a circumferential side surface radially facing the main axis, the protrusion having a circumferential side surface sized and shaped to geometrically match the side surface of the cavity, wherein:
   the main body of the one or more caps further comprises a first material component, the main body of further one or more caps comprises a second material component, and the first material component has a higher hardness value in comparison with the second material component,
   the one or more caps are successively arranged in an alternating fashion, such that the protrusion that is provided with the first material component is engaged with the cavity that is provided with the second material component, or the protrusion that is provided with the second material component is engaged with the cavity that is provided with the first material component.

10. The assembly according to claim 9, wherein the side surface of the protrusion includes a circumferential radial extension, and the side surface of the cavity includes a corresponding circumferential radial recess geometrically matching with said extension.

11. A cap for being removably attached to a septum of a needle-free intravascular connector, comprising:
   a main body comprising:
      a protrusion at a first end;
      a cavity; and
      an opening at a second end distal to the first end with regard to a main axis, for provision of access into the cavity,
   the cavity having a circumferential side surface radially facing the main axis, the protrusion having a circumferential side surface sized and shaped to geometrically match the side surface of the cavity, wherein
   the second end of the cap is provided with one or more circular ridges or grooves around the opening, that extend parallel to a main axis,
   and the main body is provided with one or more corresponding ridges or grooves that have respective shapes and sizes for geometrically matching and axially engaging with the one or more circular ridges or grooves around the opening of an identical cap, wherein: the main body of the cap further comprises a first material component and a second material component that are integrated with each other, and the first material component has a higher hardness value in comparison with the second material component, and
   the main body is arranged such that the second material component is radially compressed by the first material component when the cap is engaged with a further and identical cap by an interpenetration between the protrusion and respective cavity.

12. The cap according to claim 11, wherein the side surface of the protrusion includes a circumferential radial extension, and the side surface of the cavity includes a corresponding circumferential radial recess geometrically matching with said extension.

13. An assembly of a plurality of caps according to claim 11.

14. An assembly of one or more caps for being removably attached to a septum of a needle-free intravascular connector, each cap having a main body that comprises:
   a protrusion at a first end,
   a cavity,
   an opening at a second end distal to the first end with regard to a main axis, for provision of access into the cavity,
   the cavity having a circumferential side surface radially facing the main axis, the protrusion having a circumferential side surface sized and shaped to geometrically match the side surface of the cavity, wherein
   opposing surfaces of successively arranged couples of caps are circumferentially provided with one or more adhesives or sealants around the main axis,
   wherein: the main body of the one or more caps further comprises a first material component, the main body of further one or more caps comprises a second material component, and the first material component has a higher hardness value in comparison with the second material component,
   the one or more caps are successively arranged in an alternating fashion, such that a protrusion that is provided with the first material component is engaged with a cavity that is provided with the second material component, or a protrusion that is provided with the second material component is engaged with a cavity that is provided with the first material component.

15. An assembly of one or more caps for being removably attached to a septum of a needle-free intravascular connector, each cap having a main body that comprises:
   a protrusion at a first end,
   a cavity,
   an opening at a second end distal to the first end with regard to a main axis, for provision of access into the cavity,
   the cavity having a circumferential side surface radially facing the main axis, the protrusion having a circumferential side surface sized and shaped to geometrically match the side surface of the cavity, wherein
   one or more couples of successively arranged caps are provided with one or more removable covers that are sized and shaped for circumferentially contacting said couple of caps and covering a junction between one or more successively arranged caps, wherein: the main body of the one or more caps further comprises a first material component, the main body of further one or more caps comprises a second material component, and the first material component has a higher hardness value in comparison with the second material component,
   the one or more caps are successively arranged in an alternating fashion, such that a protrusion that is provided with the first material component is engaged with a cavity that is provided with the second material component, or a protrusion that is provided with the second material component is engaged with a cavity that is provided with the first material component.

16. The assembly according to claim 15, wherein the one or more covers are in the form of removable belts, each having a size and shape for circumferentially covering a respective junction between two caps that are engaged to one another.

17. The assembly according to claim 15, wherein the one or more covers are sized and shaped for circumferentially contacting a plurality of couples of caps and for covering a respective plurality of junctions between said plurality of couples of caps.

18. The assembly according to claim 15, wherein the one or more covers are provided with one or more series of perforations.

19. The assembly according to claim 15, wherein the one or more covers are provided with one or more circumferential series of perforations around the main axis, arranged in-between successively arranged junctions.

20. The assembly according to claim 15, wherein an inner surface of the one or more covers that faces the caps is provided with an adhesive layer for removably adhering the cover to the caps.

\* \* \* \* \*